United States Patent
Høie

(10) Patent No.: US 6,509,043 B1
(45) Date of Patent: Jan. 21, 2003

(54) COMPOSITION COMPRISING SOY PROTEIN, DIETARY FIBRES AND A PHYTOESTROGEN COMPOUND AND USE THEREOF IN THE PREVENTION AND/OR TREATMENT OF PULMONARY DISEASES

(75) Inventor: Lars Henrik Høie, London (GB)

(73) Assignee: Nutri Pharma ASA, Oslo (NO)

(*) Notice: Subject to any disclaimer, the term of this patent is extended or adjusted under 35 U.S.C. 154(b) by 0 days.

(21) Appl. No.: 09/856,884

(22) PCT Filed: Nov. 25, 1999

(86) PCT No.: PCT/IB99/01997

§ 371 (c)(1), (2), (4) Date: Aug. 15, 2001

(87) PCT Pub. No.: WO00/30664

PCT Pub. Date: Jun. 2, 2000

(51) Int. Cl.$^7$ .................. A61K 35/78; A01N 43/40; A01N 25/00
(52) U.S. Cl. .................. 424/757; 514/343; 514/825; 514/853
(58) Field of Search .................. 424/757; 514/343, 514/825, 853

(56) References Cited

U.S. PATENT DOCUMENTS

| | | | |
|---|---|---|---|
| 4,557,927 A | | 12/1985 | Miyake et al. |
| 4,591,600 A | | 5/1986 | Creuzet et al. |
| 4,818,558 A | | 4/1989 | Hartman et al. |
| 4,841,077 A | | 6/1989 | Ito et al. |
| 4,960,908 A | | 10/1990 | Ito et al. |
| 5,223,285 A | * | 6/1993 | DeMichele et al. |
| 5,320,949 A | | 6/1994 | Shen |
| 5,352,384 A | | 10/1994 | Shen |
| 5,498,631 A | | 3/1996 | Gorbach et al. |
| 5,516,528 A | | 5/1996 | Hughes et al. |
| 5,589,182 A | | 12/1996 | Tashiro et al. |
| 5,637,561 A | | 6/1997 | Shen et al. |
| 5,637,562 A | | 6/1997 | Shen et al. |
| 5,654,011 A | | 8/1997 | Jackson et al. |
| 5,698,256 A | | 12/1997 | Stilling |
| 5,702,752 A | | 12/1997 | Gugger et al. |
| 5,855,892 A | | 1/1999 | Potter et al. |
| 5,892,043 A | * | 4/1999 | Tsujihara et al. |
| 5,948,814 A | * | 9/1999 | Hwang et al. |
| 6,153,629 A | * | 11/2000 | Hoie |

FOREIGN PATENT DOCUMENTS

| | | | |
|---|---|---|---|
| EP | DW 1993-184459 | * | 6/1993 |
| EP | 0827698 | | 9/1997 |
| EP | 0898900 | | 3/1998 |
| EP | 0647408 | | 12/1999 |
| FR | 2395288 | | 6/1977 |
| JP | 1258669 | | 4/1988 |
| JP | 08064368 | | 3/1996 |
| WO | 93 23069 | | 5/1993 |
| WO | 95 10512 | | 9/1994 |
| WO | WO95 10529 | | 9/1994 |
| WO | WO95 10530 | | 9/1994 |
| WO | WO96 10341 | | 10/1995 |
| WO | WO97 07811 | | 8/1996 |
| WO | WO 98 31546 | | 2/1997 |
| WO | WO 97 37547 | | 4/1997 |
| WO | WO 98 03084 | | 7/1997 |

OTHER PUBLICATIONS

Misra et al. (International Journal of Cancer, (May 15, 1989) 43 (5) 181–183)).*

*A Review of the Clinical Effects of Phytoestrogens*, Knight and Eden, Obstetrics & Gynecology, vol. 87, No. 5, Part 2, pp 897–904, May 1996.

*A Soy Protein Isolate Rich in Genistein and Daidzein and Its Effects on Plasma Isoflavone Concentrations, Platelet Aggregation, Blood Lipids and Fatty Acid Composition of Plasma Phospholipid in Normal Men*, Gooderham, et al., J. Nutrition, vol. 126/8, pp. 2000–2006 (1986).

*Defining Food Components and New Nutrients*, Hendrich et al., J. Nutr. 124: 1789S–1792S, 1994.

*Depression of plasma cholesterol in men by consumption of baked products containing soy protein*, Potter, et al., American Journal of Clinical Nutrition 58 (1993): 4 (Oct.).

*Effects of Tyrosine Kinase Inhibitors on Antigen Challenge of Guinea Pig Lung in Vitro*, Wong, et al., The Journal of Pharmacology and Experimental Therapeutics, vol. 283, No. 1, 1997, pp. 131–137.

*Intake of 25g of Soybean Protein with or without Soybean Fiber Alters Plasma Lipids in Men with Elevated Cholesterol Concentrations*, Bakhit, et al., J. Nutr. 124: 213–222, 1994.

*Lipoprotein Heterogeneity and Apolipoprotein B Metabolism*, Packard and Shepherd, Arteriosclerosis, Thrombosis, and Vascular Biology, vol. 17, No. 12, Dec. 1997, pp 3542–3556.

*Long–Term Treatment of Hypercholesterolemia With Dietary Fiber*, Hunninghake, et al., The American Journal of Medicine, vol. 97, pp 504–508, Dec. 1994.

*Meta–analysis of the Effects of Soy Protein Intake on Serum Lipids*, Anderson, et al., The New England Journal of Medicine, vol. 333, No. 5, pp 276–282, Aug. 3, 1995.

(List continued on next page.)

Primary Examiner—Christopher R. Tate
Assistant Examiner—Randall Winston
(74) Attorney, Agent, or Firm—Gabor L. Szekeres

(57) ABSTRACT

A composition comprising (a) soy protein, (b) a phytoestrogen compound, and (c) dietary fibers. The soy protein (a) is present in an amount of at least 45 weight percent of the total protein content of the composition, said total protein content providing at least 15% of the total energy content of the composition. The phytoestrogen compound (b) is preferably a naturally occurring isoflavone and is present in an amount of more than 0.10 weight percent of the soy protein, and the dietary fibers (c) are preferably soybean fibers and are present in an amount of more than 4 weight percent of the total weight of the nutritional composition on a dry basis. The composition is useful for treating pulmonary diseases.

6 Claims, No Drawings

OTHER PUBLICATIONS

*Modern Applications for an Ancient Bean: Soybeans and the Prevention and Treatment of Chronic Disease*, Messina, J. Nutr. 125:567S–569S, 1995.

*New Trends in Atherosclerotic Research*, Faggiotto, Atherosclerosis Reviews, vol. 21, pp 187–194 (1990).

*Phytoestrogen Content of Foods—A Compendium of Literature Values*, Reinli and Block, Nutrition and Cancer 1996.

*Phytoestrogens—a short review*, Knight and Eden, Maturitas 22, Journal of the Climacteric and Postmenopause, pp 167–175 (1995).

*Phyto–oestrogens and Western Diseases*, Adlecreutz and Mazur, The Finnish Medical Society DUODECIM, Ann. Med. 29, 95–120 (1997).

*Putting Low–Density Lipoproteins at Center Stage in Atherogenesis*, Sniderman, et al., The American Journal of Cardiology, vol. 79, Jan. 1, 1997.

*Soy Containing Isolfavones Reduces Cholesterol*, Crouse and Burke, Abstract for presentation at the American Heart Association, Mar. 1998.

*Soy isoflavones enhance coronary vascular reactivity in atherosclerotic female macaques*, Honore et al, Fertility and Sterility, vol. 67, No. 1, pp. 148–154 (Jan. 1997).

*Soy: is this a food we could be encouraging in diabetes?*, Govindji, Practical Diabetes International, vol. 15, No. 5, Sep. 1998, pp. 163–164.

*Soy protein and serum lipids*, Potter, Current Opinion in Lipidology 1996, 7, pp. 260–264.

* cited by examiner

COMPOSITION COMPRISING SOY PROTEIN, DIETARY FIBRES AND A PHYTOESTROGEN COMPOUND AND USE THEREOF IN THE PREVENTION AND/OR TREATMENT OF PULMONARY DISEASES

FIELD OF THE INVENTION

The present invention relates to soy protein, phytoestrogens and dietary fibres and compositions thereof suitable for preventing, alleviating and/or treating pulmonary diseases. The compositions are particularly useful in treating e.g. chronic obstructive pulmonary disease (COPD), inflammation of the airways, asthma, bronchoconstriction, bronchitis, and small airways disease. The present invention also relates to the use of these compositions as a medicament and/or in the manufacture of a medicament for treating a subject suffering from a pulmonary disease, more particularly chronic obstructive pulmonary disease (COPD), inflammation of the airways, asthma, bronchoconstriction, bronchitis, and/or small airways disease. The present invention also concerns use of a composition according to the present invention in the prevention and/or treatment of said diseases and disorders. In addition, the present invention also provides methods for preventing and/or treating and/or prophylactically treating and/or alleviating by therapy said diseases and disorders.

BACKGROUND OF THE INVENTION

The airways of the human and animal body consist of a series of tubes and passages that include the throat, the larynx and the trachea. In the chest cavity the trachea divides into the right and left bronchi, or bronchial tubes, that enter the lungs. The branches of the bronchi subsequently become more narrow and form tubes, the bronchioles, that divide into even more narrow tubes, the alveolar ducts. The end of each alveolar duct forms a cluster of thinly walled sacs termed the alveoli.

Pulmonary diseases are diseases generally affecting the lungs. The airways and the lungs are subject to many disease causing and/or disease stimulating factors such as e.g. inhaled pathogens like bacteria and viruses, allergens and toxic substances such as cigarette smoke or air pollutants. Such factors generate disorders with symptoms like e.g. difficulty in breathing, chest pains, coughing, and wheezing.

Several terms have been used to describe a group of conditions now generally recognized as leading to a limitation or obstruction of the flow of air in the airways and in the lungs. Obstructive pulmonary disease (OPD) and chronic obstructive pulmonary disease (COPD) are clinical terms describing diseases characterized by an obstruction or limitation of airflow during expiration. For COPD the obstruction or limitation is persistent. The terms represent a clinical rather than a pathological diagnosis and relate to diseases such as e.g. inflammation of the airways, asthma, bronchitis, and small airways diseases. However, the nomenclature in the field of obstructive pulmonary diseases is complex and sometimes confusing in spite of many attempts to define conditions such as asthma and bronchitis.

It is widely recognized that COPD is not a disease entity, but rather a complex of conditions characterized by airflow limitation or obstruction. The limitation or obstruction may be variable over short periods of time and reversible, even though an underlying irreversible trait may persist. Unless treated, the disease is likely to progress and lead to a seriously reduced airflow limitation. This reduction is usually, but not always, persistent and typically shows a more rapid progressive deterioration with age than normal. Clinical studies of acute exacerbations of obstructive pulmonary diseases are difficult because of i) the heterogeneous nature of COPD, ii) diffuse symptoms that can vary spontaneously, and iii) difficulties in defining a clinical response both in the short term and in the long run. Also, the role of e.g. bacterial infections and the subsequent use of antibiotics in connection with pulmonary diseases is controversial, and much evidence shows that although bacterial infections have a significant role in acute exacerbation, the role of said infections in the progression of obstructive pulmonary diseases is less certain.

Accordingly, any of the above-mentioned conditions—whether transient or chronic—may result in an airflow limitation or obstruction and may therefore be potentially associated with obstructive pulmonary diseases. The conditions may, however, also be present anatomically without generating an impairment of pulmonary function that is sufficient to qualify for the definition OPD or COPD.

An obstruction of the airways is measured by $FEV_1$ as forced expiratory volume in the first second of expiration. Lung function measured as the $FEV_1$ increases into young adulthood and then it starts to decrease. In normal non-smokers, the rate of decline in $FEV_1$ is about 20 ml per year, i.e. about 1 liter over a 50-year period. A much more rapid decline is observed in smokers. On average, the decline is twice that of normal non-smokers. However, in about 15% of all smokers, lung function declines at a rate much more rapid than the decline observed in the average smoker. Consequently, airways diseases are strongly influenced by individual rates of decline in $FEV_1$.

Asthma has traditionally been regarded as a respiratory disease of acute airway obstruction, and research as well as therapeutic attention has focused principally on the mechanisms leading to acute bronchospasm. One of the conventional therapies has consisted of bronchodilators to regulate airway smooth muscle contraction. However, current state of the art asthma therapy does have side effects, mostly due to undesirable effects from the inhalation steroids used.

A wide range of pharmaceuticals have been developed by the pharmaceutical industry and evaluated in clinical trials. Although being capable of inhibiting mast cell-mediated acute allergic bronchoconstriction, none of these pharmaceuticals are suitable for use in a prophylactical treatment or maintenance treatment of asthma. Medicaments such as $\beta_2$ agonists have been introduced in order to treat airways diseases and in particular asthma. $\beta_2$ agonists inhibit the release of histamine into the circulation of asthmatics undergoing an allergen provocation. This pharmacological property may contribute to the well-recognized ability of $\beta_2$ agonists to inhibit allergen-induced bronchoconstriction. However, while $\beta_2$ agonists are exceptional mast cell stabilizing agents, sole therapy with these agents may actually enhance hyperresponsiveness of airways to exogenous stimuli such as inhaled histamine, most likely due to a minimal effect on airway inflammation.

Widespread use of $\beta_2$ agonists have lead to a criticism based on a hypothesis involving the so-called "asthma paradox". According to the hypothesis, $\beta_2$ agonists have undesirable effects on the normal role of mast cell degranulation as an endogenous anti-inflammatory mechanism to prevent antigens from entering the lower airways and limit the extent of the subsequent repair process.

Adlercreutz (Finnish Medical Society, Ann. Med. 29,95–120 (1997)) has reviewed the phytoestrogen classes of lignans and isoflavones and has described their influences on a range of cellular activities and metabolic events. It is stated that despite an abundant literature at this early stage of dietary phytoestrogen research, much work is needed before any recommendation as to phytoestrogen consumption can be made. However, experimental and epidemiological evidence does support the view that these compounds do not have any negative effects and that they may form a group of substances with a great potential in preventive medicine. It is emphasised that at present, no definite recommendations can be made as to the dietary amounts needed for disease prevention. No reference is made to a composition comprising a combination of soy protein, a high content of a phytoestrogen compound, and dietary fibres. Gooderham (J. Nutr. 126(8), 2000–2006 (1996)) has suggested that although soy protein supplementation to a typical Western diet may increase plasma concentrations of isoflavones, this may not necessarily be sufficient to counter disease risk factors. Increases in serum levels of isoflavones following a soy rich diet were found to be quite variable among analysed subjects. This was thought to be due to e.g. the timing of the soy protein consumption or the composition of the gut flora. The metabolism of isoflavones in the gut is variable among individuals and remains to be elucidated. It is stressed that the isoflavones in human plasma predominantly exist in the inactive glucuronide conjugated form, and only a small amount such as approx. 10 percent exists in the active free and sulphate conjugated forms. No reference is made to a composition comprising a combination of soy protein, a high content of a phytoestrogen compound, and dietary fibres.

Hendrich (J. Nutr. 124(9Suppl.), 1789S–1792S (1994)) has reported that isoflavones may be of great potential benefit to human health maintenance and that isoflavones may be health-protective in amounts potentially available from a human diet containing daily soy foods. The food content of isoflavones is in the range of from 0.1 to 1 mg/g in soy foods. Several factors such as variety of soybean, processing and the addition of other ingredients to the food influence isoflavone contents of foods. It is stated that human intestinal bacteria can destroy ingested isoflavones to a great extent and that this may be why only 15 to 20 percent of isoflavones are reported to be recoverable in intact form from the urine and faeces. It is emphasised that much work remains to determine the relation between concentration of isoflavones in human urine and plasma and the biological effects of the isoflavones. It is noted that although more health-related animal data need to be obtained, the time is approaching when long-term human feeding trials of purified isoflavones and foods containing isoflavones to examine health-related outcomes may be warranted. No reference is made to a composition comprising a combination of soy protein, a high content of a phytoestrogen compound, and dietary fibres.

Knight (Maturitas 22, 167–175 (1995)) provides a synopsis of the literature relating principally to the clinical effects of phytoestrogens on the diseases associated with ageing. It is concluded that isoflavones represent a large and exciting group of compounds with potential benefits to many diseases. No reference is made to a composition comprising a combination of soy protein, a high content of a phytoestrogen compound, and dietary fibres.

Knight (Obstet. Gynecol. 87, 897–904 (1996)) has reviewed the sources, metabolism, potencies, and clinical effects of phytoestrogens on humans. The review suggests that phytoestrogens are among the dietary factors affording protection against heart disease in vegetarians. Based on epidemiologic and cell line studies, it is emphasised that intervention studies are now an appropriate consideration to assess the clinical effects of phytoestrogens because of the potentially important health benefits associated with the consumption of foods containing these compounds. It is concluded that clinical applications for phytoestrogens are still in their infancy. No reference is made to a composition comprising a combination of soy protein, a high content of a phytoestrogen compound, and dietary fibres.

Reinli (Nutr. Cancer 26, 123–148 (1996)) has reviewed the literature for quantitative data on the levels of known phytoestrogens (daidzein, genistein, coumestrol, formononetin and biochanin A) in food plants. It is reported that the isoflavones daidzein and genistein may exist in four related chemical structures, i.e. an aglycone structure (daidzein and genistein), a 7O-glucoside structure (daidzin and genistin), a 6'-O-acetylglucoside structure (6'-O-acetyidaidzin and 6'-O-acetylgenistin), and a 6'-O-malonylglucoside structure (6'-O-malonyidaidzin and 6'-O-malonylgenistin). The conjugates (7-O-glucosides, 6'-O-acetylglucosides, and 6'-O-malonylglucosides) are transformed to aglycones, which are sometimes called free isoflavones, through hydrolysis in the intestinal tract by β-glucosidase enzymes of gut bacteria. Acid hydrolysis in the stomach may also contribute to the formation of free isoflavones. It is unclear how readily conjugates undergo intestinal hydrolysis and subsequent absorption. It is stressed that isoflavones are metabolised differently by different animals and humans. No reference is made to a composition comprising a combination of soy protein, a high content of a phytoestrogen compound, and dietary fibres.

WO 95/10512 relates to a process for producing an aglucone isoflavone enriched vegetable protein whey and discloses in one embodiment a whey having a dry basis genistein content of about 2.6 to about 8.7 mg/gram and a dry basis daidzein content of about 2.5 to about 6.0 mg/gram. No reference is made to a treatment of a pulmonary disease by using a composition comprising a combination of soy protein, a high content of a phytoestrogen compound, and dietary fibres. No reference is made to a composition comprising a combination of soy protein, a high content of a phytoestrogen compound, and dietary fibres.

WO 95/10529 relates to a process for producing an aglucone is isoflavone enriched protein concentrate and discloses in one embodiment a concentrate having on a dry basis a genistein content of about 1.0 to about 2.0 mg/gram and a daidzein content of about 0.7 to about 1.5 mg/gram. No reference is made to a treatment of a pulmonary disease by using a composition comprising a combination of soy protein, a high content of a phytoestrogen compound and dietary fibres. No reference is made to a composition comprising a combination of soy protein, a high content of a phytoestrogen compound, and dietary fibres.

WO 95/10530 relates to a process for producing an aqueous extract comprising protein and glucone isoflavones and discloses in one embodiment a vegetable protein isolate having a dry basis genistein content of about 1.5 to about 3.5 mg/gram and a dry basis daidzein content of about 1.0 to about 3.0 mg/gram. No reference is made to a treatment of a pulmonary disease by using a composition comprising a combination of soy protein, a high content of a phytoestrogen compound, and dietary fibres. No reference is made to a composition comprising a combination of soy protein, a high content of a phytoestrogen compound, and dietary fibres.

WO 97/31546 discloses data from total replacement programmes (for 6 weeks) in weight reduction studies conducted at Karolinska Hospital in Sweden. It is shown that products with isolated soy protein and soy cotyledon fibres reduce serum triglyceride levels by a maximum of 44 percent and cholesterol levels by a maximum of 33 percent for a patient population a with mean initial cholesterol content of 6.25 mmol/l. No reference is made to a treatment of a pulmonary disease by using a composition comprising a combination of soy protein, a high content of a phytoestrogen compound, and dietary fibres. No reference is made to a composition comprising a combination of soy protein, a high content of a phytoestrogen compound, and dietary fibres.

WO 97/37547 discloses an isoflavone-enriched soy protein product having a protein content greater than 60 percent of total dry matter, a total dietary fibre content of less than 4 percent of total dry matter, a sucrose content greater than 10 percent of total dry matter, a total content of sulphur-containing amino acids greater than 2.2 percent of the total amino acid content, a stachyose content of less than 1.5 percent of total dry matter, and a total isoflavone content greater than 2.5 mg/gram, equivalent to 0.25 percent. The use of soy cotyledon fibres is not anticipated and the claimed invention is for use as an ingredient in the production if an edible-product and not in a treatment of pulmonary diseases. Also, the product differs from the present invention by comprising total dietary fibre in an amount of less than 4 percent of total dry matter, by containing an unusually low amount of stachyose and a high amount of sulphur-containing amino acids. No reference is made to a treatment of a pulmonary disease by using a composition comprising a combination of soy protein, a high content of a phytoestrogen compound, and dietary fibres.

U.S. Pat. No. 5,320,949 discloses a process for producing an aglucone isoflavone enriched fibre from a vegetable protein material in the form of a slurry and discloses in one embodiment an aglucone enriched fibre product directly obtainable from said process and having a genistein content of about 1.0 and 2.0 mg/gram and a daidzein content of about 0.7 to 1.7 mg/gram. No reference is made to a treatment of a pulmonary disease by using a composition comprising a combination of soy protein, a high content of a phytoestrogen compound, and dietary fibres. No reference is made to a composition comprising a combination of soy protein, a high content of a phytoestrogen compound, and dietary fibres. No reference is made to a composition comprising soy cotyledon fibres and a phytoestrogen compound.

U.S. Pat. No. 5,352,384 discloses an aglucone enriched fibre product having a genistein content of about 1.0 and 2.0 mg/gram and a daidzein content of about 0.7 to 1.7 mg/gram. No reference is made to a treatment of a pulmonary disease by using a composition comprising a combination of soy protein, a high content of a phytoestrogen compound, and dietary fibres. No reference is made to a composition comprising a combination of soy protein, a high content of a phytoestrogen compound, and dietary fibres.

EP 827 698 A2 and EP 827 698 A3 disclose a process for producing an aglucone isoflavone enriched extract from a vegetable material containing isoflavone conjugates and protein. No reference is made to a treatment of a pulmonary disease by using a composition comprising a combination of soy protein, a high content of a phytoestrogen compound and dietary fibres. No reference is made to a composition comprising a combination of soy protein, a high content of a phytoestrogen compound, and dietary fibres.

An abstract presented at the American Heart Association's $38_{th}$ Annual Conference on Cardiovascular Disease Epidemiology and Prevention held in March 1998 disclosed a diet supplemented with 25 grams of soy protein containing 4 mg, 25 mg, 42 mg, and 58 mg of isoflavone, respectively. No reference is made to a treatment of a pulmonary disease by using a composition comprising a combination of soy protein, a high content of a phytoestrogen compound and dietary fibres. No reference is made to a composition comprising a combination of soy protein, a high content of a phytoestrogen compound, and dietary fibres.

SUMMARY OF THE INVENTION

The present invention provides a nutritional composition having a fixed, high amount of a phytoestrogen compound such as e.g. naturally occurring isoflavones. More particularly the present invention provides a nutritional composition of soybean extractable ingredients having a high, fixed amount of a phytoestrogen compound such as e.g. naturally occurring isoflavones.

The present invention represents a new approach to treatment of pulmonary diseases and provides a nutritional composition comprising a) soy protein, preferably isolated soy protein, b) a high, fixed content of a plant hormone in the form of a phytoestrogen compound, such as e.g. naturally occurring isoflavones, and c) dietary fibres, preferably soybean fibres, more preferably soybean fibres manufactured from the cotyledon of soybeans hereinafter referred to as soy cotyledon fibres.

The present invention is useful in the prevention and/or effective treatment of pulmonary diseases such as e.g. airway inflammation, asthma, bronchitis and small airways diseases, in particular asthma including chronic asthma such as e.g. asthma characterised by a chronic inflammatory condition. The present invention is believed to be capable of increasing $FEV_1$ of a subject, measured by forced expiratory volume in the first second of expiration, as well as being capable of treating, alleviating and/or eliminating in particular i) inflammation of the airways, ii) mucus hypersecretion, and iii) bronchoconstriction. A composition according to the present invention may be comprised in a micronutrient as defined herein below.

Phytoestrogen compounds are naturally occurring plant hormones showing a structural similarity to 17β-estradiol. Phytoestrogens consist of a number of classes including isoflavones, coumestans, lignans and resorcylic acid lactones. The class of isoflavones consists of among others genistein, daidzein, equol, glycitein, biochanin A, formononetin, and O-desmethylangolesin. The isoflavones genistein and daidzein are found almost uniquely in soybeans. When present in the plant the isoflavones are mainly in a glucoside form, i.e. attached to a sugar molecule. Isoflavones in this glucoside form can be deconjugated to yield isoflavones in a so-called aglycone form, which is the biologically more active form of isoflavones and which is absorbed faster and to a greater extent in the human gut than isoflavones in the glucoside form. In vitro studies have examined the relative estrogenic effect exerted by various phytoestrogens including isoflavones. The resulting potencies as compared to estradiol (having a relative potency of 100), have been reported by Knight (Maturitas 22, 167–175 (1995)) for among others genistein (0.084) and daidzein (0.013). However, the results also showed that the estrogen receptor complexes formed by estradiol and isoflavones such as genistein and daidzein are functionally equivalent. The comparative dissociation constant of genistein for the estrogen receptor, as determined in competitive binding assays, was found to be from 100 to 10.000 times higher than that of estradiol.

The term "naturally occurring" substance as used in the present specification and the appended claims refers to a substance originally isolated from a natural source, such as an animal or a plant, for example a soy plant, or modified forms of such a sub-stance. The naturally occurring substance for use in a composition according to the present invention may be included in the composition as part of the natural source or in any type of extract, isolate or the like thereof, or it may have been isolated from a plant source or synthesized biologically, microbiologically, or chemically or by any other means.

Accordingly, in one aspect the present invention provides a composition comprising (a) a soy protein source, selected from isolated soy protein, soy protein concentrate, or soy flour, said soy protein source providing an amount of soy protein, which is at least 45 weight percent of the total protein content of the composition, said total protein content providing at least 15 percent of the total energy content of the composition, (b) at least one phytoestrogen compound in an amount of more than 0.10 weight percent of the soy protein content of the composition, and (c) dietary fibres in an amount of more than 4 weight percent of the total weight of the composition on a dry basis.

In a more preferred aspect the present invention provides a composition comprising (a) isolated soy protein in an amount of at least 50 weight percent of the total protein content of the composition, said total protein content providing at least 15 percent of the total energy content of the composition, (b) at least one phytoestrogen compound in an amount of more than 0.10 weight percent of the soy protein content of the composition, and (c) soybean fibres in an amount of more than 4 weight percent of the total weight of the composition on a dry basis.

In a most preferred aspect the present invention provides a composition comprising (a) isolated soy protein in an amount of at least 50 weight percent of the total protein content of the composition, said total protein content providing at least 15 percent of the total energy content of the composition, (b) at least one phytoestrogen compound in an amount of more th an 0.10 weight percent of the soy protein content of the composition, and (c) soy cotyledon fibres in an amount of more than 4 weight percent of the total weight of the composition on a dry basis.

Phytoestrogen compounds according to the present invention are defined as naturally occurring plant substances, said substances being either structurally or functionally similar to 17β-testradiol or generating estrogenic effects. Phytoestrogens consist of a number of classes including isoflavones, coumestans, lignans and resorcylic acid lactones. Examples of isoflavones according to the present invention are genistein, daidzein, equol, glycitein, biochanin A, formononetin, and O-desmethylangolesin. The phytoestrogen compounds of a composition according to the present invention are preferably isoflavones, more preferably genistein, daidzein, glycitein and/or equol yet more preferably genistein, and/or daidzein and even more preferably genistein. Genistein and daidzein are found almost uniquely in soybeans. A preferred composition according to the present invention may accordingly comprise a single isoflavone, such as genistein, daidzein, glycitein or equol, or it may comprise at least one isoflavone selected from the group consisting of at least genistein, daidzein, glycitein and equol.

In one embodiment the present invention provides a composition according to the present invention for use as a medicament. The use of a composition according to the present invention in the manufacture of a medicament for treating a subject suffering from pulmonary diseases represents another embodiment of the present invention. Such a medicament may be effective in preventing and/or treating a pulmonary disease such as e.g. a disease selected from the group consisting of inflammation of the airways, bronchoconstriction, bronchitis, asthma, and small airways diseases.

The present invention also provides a method of preventing, alleviating and/or treating by therapy a pulmonary disease in a human or animal body, said method comprising administration of a composition according to the present invention in an amount effective in treating, alleviating and/or preventing inflammation of the airways and/or bronchoconstriction and/or bronchitis and/or asthma and/or small airways diseases.

According to another embodiment the present invention provides a method of preventing, alleviating and/or treating by therapy a pulmonary disease in a human or animal body, said method comprising administration of a composition according to the present invention in an amount effective in reducing and/or eliminating mucus hypersecretion and/or dyspnea of a subject and/or increasing $FEV_1$ as measured by forced expiratory volume in the first second of expiration.

Obstructive pulmonary disease (OPD) including chronic obstructive pulmonary disease (COPD) as used herein is:defined as a condition comprising subjects with airways limitations or obstructions or subjects with a mucus hypersecretory condition including chronic mucus hypersecretion, i.e. subjects with asthma including chronic asthma and subjects with bronchitis including chronic bronchitis. However, a clear distinction between e.g. bronchial asthma and chronic bronchitis can be difficult and sometimes impossible to make, and a sharp distinction between COPD and OPD is therefore not always possible.

Mucus hypersecretion and a limited or obstructed airflow are two major characteristics of COPD. According to one presently preferred theory, mucus hypersecretion is an initial mechanism that leads to recurrent respiratory infections, that in turn generates a destruction of the airways' and promotes a development of pulmonary parenchyma and airflow obstruction. At least two separate conditions, i) mucus hypersecretion and ii) dyspnea, are identifiable due to an obstructive or limited lung function. Chronic mucus hypersecretion and obstructive airflow are not necessarily related, since an individual may have a hypersecretory disorder only, or an obstructive disorder only, or both a hypersecretory and an obstructive disorder. Chronic mucus hypersecretion is associated with an impaired mucociliary clearance and may therefore predispose to lung cancer by causing a prolonged contact between potential carcinogens with the bronchial epithelium. Accordingly, a composition according to the present invention may be effective in treating and/or alleviating mucus hypersecretion and dyspnea in a subject.

Asthma as used herein is:defined as a respiratory disease in which spasm and constriction of the bronchial passages and swelling of their mucous lining cause obstruction of breathing, often, but not exclusively, due to allergy. One mechanism for expiratory airflow limitation in asthma is a smooth muscle contraction leading to a narrowing of the airway lumen. Asthma is frequently divided clinically into extrinsic and intrinsic asthma, separating asthma triggered by environmental allergens from that in which atopy does not appear to play a major role. Consequently, a composition according to the present invention may be effective in preventing, treating and/or alleviating smooth muscle contraction.

In asthma the airways are occluded by tenacious plugs of exudate and mucus, and there occurs a fragility of airway surface epithelium, thickening of the reticular layer beneath the epithelial basal lamina, bronchial vessel congestion and edema. An increased inflammatory infiltrate comprising "activated" lymphocytes and eosinophils, and an enlargement of bronchial smooth muscle, particularly in medium-sized bronchi, is also observed. Asthma comprises at least extrinsic (atopic or allergic) and intrinsic (non-atopic) divisions, each of which present clinically in a variety of ways. A composition according to the present invention may be effective in preventing and/or alleviating the formation of tenacious plugs of exudate and mucus, effective in preventing, alleviating or treating a fragility of airway surface epithelium subsequently generated by mucus secretion, effective in preventing, reducing or eliminating any thickening of the reticular layer beneath the epithelial basal lamina, and effective in preventing, alleviating or treating bronchial vessel congestion and/or edema.

Asthma may in some cases be regarded as a chronic inflammatory disease. Since the term chronic asthmatic bronchitis has no clearly defined pathologic equivalent, patients having a chronic productive cough normally associated with chronic bronchitis, as well as bronchospasms, at the same time as having an airflow obstruction, will be regarded as suffering from both chronic bronchitis as well as small airways disease (chronic obstructive bronchitis) and asthma, since the pathology presumably would be that of those conditions.

A composition according to the present invention may be effective in preventing, alleviating and/or curing inflammation of the airways, whether transient or chronic. Airway inflammation is thought to be an important contributor to asthma, and airway inflammation may well be present even in the absence of severe symptoms of asthma. In one particularly preferred aspect the present invention provides a treatment and/or alleviation of an inflammation of the airways by means of an anti-oxidative effect exerted by a composition according to the present invention. The anti-oxidative effect is exerted in particular by naturally occurring isoflavones forming part of a composition according to the present invention.

A composition according to the present invention may be effective in increasing $FEV_1$, as measured by forced expiratory volume in the first second of expiration, said effect being exerted by the binding of a component of the composition, particularly a naturally occurring isoflavone, to a beta-2-receptor or a receptor belonging to the class of beta-2-receptors. Beta-2-receptors are present on many different types of cells including cells in airways and vessels. A composition according to the present invention may also be effective in generating a dilatation of the airways in a subject, preferably a subject suffering from a pulmonary disease.

The occurrence of bronchial inflammation in asthma is, according to one presently preferred hypothesis, thought to arise at least in part from an airway response to an antigen in an allergic subject. The response includes immediate pulmonary mast-cell activation and initiation of an inflammatory response that develops over hours and is important in the later and more persistent development of bronchial obstruction. A composition according to the present invention may be effective in treating, alleviating and/or eliminating several of the causes of airway obstruction that—alone or in combination—contributes to bronchial hyperresponsiveness, i.e. the fundamental defect in asthma. Importantly, airway inflammation is believed to be a crucial component for i) the chronicity of asthma, ii) the intensity of airways hyperresponsiveness, and iii) the absence of a complete therapeutic control, when bronchodilator therapy is used alone. Consequently, a composition according to the present invention may be effective in controlling, reducing and/or eliminating edema, mucus secretion, and inflammation of the airways resulting at least in part from a response to an allergen.

Although the precise pathogenesis of asthma has yet to be discovered, allergic reactions and respiratory infections are particularly important. Both are frequent factors in asthma and exacerbations of asthma, and both not only trigger acute asthmatic symptoms but may also enhance the degree of airway hyperresponsiveness long after the initial stimulus has been removed. Of particular interest has been the airway's response to an inhaled antigen. Almost all subjects with allergic asthma experience immediate bronchospasm following inhalation of an antigen, i.e. acute airway obstruction, within 15 min of antigen exposure. In these subjects, antigen inhalation initiates not only immediate bronchocontraction, but also the reappearance of airway obstruction 4 to 6 hours later, a condition known as late asthmatic reaction or LAR. The late asthmatic response has a number of features that are characteristic of chronic asthma such as e.g. less responsiveness to bronchodilator therapy than the isolated acute event, an increased airway responsiveness, and the development of bronchial inflammation. Two features of the LAR to antigen inhalation suggest a linkage to the pathogenesis of asthma: The presence of bronchial inflammation and the enhancement of bronchial responsiveness. Consequently, a composition according to the present invention may be capable of preventing both immediate bronchocontraction as well as a late asthmatic reaction.

Asthmatic reactions following inhalation of an antigen include an immediate release from pulmonary mast cells of preformed mediators and a generation of a variety of factors needed to initiate an acute allergic airway reaction. Because the airways of patients with asthma are hyperresponsive, the immediate bronchial reaction to mast cell bronchospastic mediators is accentuated beyond the pharmacological properties of these substances. With cellular activation by antigen and membrane-bound IgE interaction, the mast cell initiates a generation of leukotrienes and prostaglandins. The leukotrienes, $C_4$, $D_4$, $E_4$, along with histamine, are undoubtedly involved in the acute bronchospastic response because of their airway smooth muscle contractile properties. The generation and release by mast cells of chemotaxic factors is important for the recruitment of inflammatory cells to the airway and for the subsequent development of the late asthmatic response. Accordingly, a composition according to the present invention may be capable of effectively reducing or eliminating mast cell mediated secretion of mediators such as e.g. heparin, histamine and sulphidopeptide leukotrienes $C_4$, $D_4$, and $E_4$.

Associated with the development of the LAR is a recruitment of inflammatory cells to the airway, including neutrophils, macrophages, lymphocytes, eosineophils, monocytes, and basophils. With their entry into the airways, and presumable cellular activation, airway obstruction reappears. It is thought that components of airway obstruction in LAR include bronchospasm, edema, and inflammation. An additional consequence of the LAR is an increase in airway hyperresponsiveness; thus, the asthmatic process is further perpetuated and positively reinforced. Consequently, a composition according to the present invention may be capable of effectively controlling in a late asthmatic response the symptoms of bronchospasm, edema, and inflammation, and in addition also effectively controlling such as reducing and/or eliminating any increase in airway hyperresponsiveness.

Furthermore, mast cells may according to another presently preferred hypothesis produce various cytokines, interleukin 3 (IL-3), interleukin 5 (IL-5), and granulocyte/macrophage colony-stimulating factor (GM-CSF), which can perpetuate the allergic reaction by further priming inflammatory cells. Consequently, a composition according to the present invention may be capable of effectively controlling i.e. reducing and/or eliminating the production of various cytokines, interleukins such as e.g. interleukin 3 (IL-3) and interleukin 5 (IL-5), and granulocyteimacrophage colony-stimulating factor (GM-CSF), and reduce any further priming of inflammatory cells during an early and/or late asthmatic response.

A class of cells termed neutrophils can be found in lavage fluid from an asthmatic subject, but the precise role of neotrophils in the generation of a late allergic reaction has not yet been established. The neutrophil cell has a potential for generating inflammation by releasing e.g. lysosomal enzymes, oxygen metabolites, leukotriene $B_4$ and by synthesising histamine-releasing factor (HRF). HRF can amplify the allergic reaction by causing mediator release from a class of cells termed basophils that also appear during a late allergic reaction. Consequently, a composition according to the present invention may be capable of effectively controlling i.e. reducing and/or eliminating a neutrophil production of e.g. lysosomal enzymes, oxygen metabolites, leukotriene $B_4$ and histamine-releasing factor (HRF).

Evidence also exists for an implication of the group of cells termed eosinophils in an asthmatic response. Circulation of eosinophils leads to an increased severity of airway obstruction. Eosinophil granular associated proteins, including major basic protein (MBP), eosinophil cationic protein, eosinophil-derived neurotoxin, and eosinophil peroxidase are known to have profound effects on airway and cell function. MBP in particular has a number of unique properties accentuating the asthmatic response. MBP can directly injure airway epithelium, promote bronchial responsiveness, and mediate smooth muscle contraction. MBP further activates the release of mediators from mast cells and basophiis. Eosinophils may also be involved in initiating tissue damage associated with various allergic diseases, such as e.g. the epithelial desquamation observed in asthmatics. This tissue damage has been suggested to be mediated in part via the release of cytotoxic mediators such as major basic protein (MBP), eosinophil cationic protein (ECP), and eosinophil peroxidase (EPO).

Eosinophil activation result's in the release of a number of important mediators, including leukotriene $C_4$, which can contract airway smooth muscle, and platelet-activating factor (PAF). The release process of PAF has not been fully defined, but if secreted, this lipid mediator could contract airway smooth muscle as well as increase bronchial responsiveness. Furthermore, PAF is a potent eosinophil chemoattractant and a functional primer. Accordingly, eosinophils possess properties directly and indirectly causing airway obstruction and promoting bronchial hyperresponsiveness. Consequently, a composition according to the present invention may be capable of effectively controlling i.e. reducing and/or eliminating any increase in the formation of eosinophils during an asthmatic response. A composition according to the present invention may further be effective in controlling the production of eosinophil granular associated proteins including major basic protein (MBP), eosinophil cationic protein, eosinophil-derived neurotoxin, and eosinophil peroxidase. In an even further embodiment, a composition according to the present invention may be effective in controlling i.e. reducing and/or eliminating the release of mediators from mast cells, neutrophils, basophils and eosinophils, in particular the release of mediators such as e.g. leukotriene $C_4$ and platelet-activating factor (PAF), IL-3, GM-CSF and IL-5.

To generate airway inflammation after eosinophil recruitment, a number of events need to occur such as e.g. eosinophil migration to the lung and eosinophil activation. The last event is likely to involve eosinophil adhesion to endothelium and, eventually, airway epithelium. Accordingly, a composition according to the present invention may be effective in preventing eosinophil participation in the bronchial responsiveness process by inhibiting eosinophil adhesion to endothelium and epithelium.

Mast cells may also release compounds such as heparin and related proteoglycans, but the release of such mediators have so far not received much attention from allergy researchers. These highly anionic molecules are normally only associated with the binding histamine within mast cell granules. These molecules may act as natural antiinflammatory molecules and, thus, have a far greater role in the pathogenesis of allergic diseases. Accordingly, a composition according to the present invention may be effective in promoting the release of potentially antiinflammatory molecules such as e.g. heparin and related proteoglycans. Also, it has been reported that another cationic protein, platelet factor 4 (PF4), is a chemotaxic agent for human eosinophils and is a molecule well recognized for its ability to bind heparin. It is therefore plausible that endogenous heparin could be released to limit both the extent of eosinophil recruitment into sites of allergic inflammation as well as the extent of tissue damage induced by cationic proteins. Lymphocytes are also likely to be involved in the pathogenesis of allergic asthma. Recent studies have suggested that heparin acts as an immunomodulator inhibiting lymphocyte activation and trafficking and, like glucocorticosteroids, can also inhibit delayed hypersensitivity responses.

Further evidence of asthma being a chronic inflammatory disease is provided by the observation that an exposure to an allergen that results in tissue damage is likely to lead to a repair of the damage. Evidence of this repair process can most likely be seen in the asthmatic lung, where a thickened basement membrane is believed to be related to subepithelial fibrosis, the presence of myofibroblasts, and collagen deposition. Also, asthma is further characterized by a thickened smooth muscle layer.

The above-mentioned changes appear very early in the disease and are not constricted to patients with chronic asthma. Furthermore, even following chronic treatment with inhaled glucocorticosteroids for periods of up 10 years, the thickness of the basement membrane is not reduced, although such therapy reduces the number of inflammatory cells present in the biopsies and the extent of the epithelial damage. Such clinical observations suggest that once these anatomic changes have appeared they may not be readily reversible, even with the most aggressive therapy currently available. Thus, it is plausible that once established, such anatomic changes may underlie the irreversible component of the disease, and by altering the geometry of the airway wall, these changes may contribute to the persistent airways hyperresponsiveness that does not respond to treatment. Accordingly, a composition according to the present invention may, in one particularly preferred embodiment, be capable of effectively preventing and/or alleviating the formation of a thickened basement membrane or a smooth muscle layer, subepithelial fibrosis, the presence of myofibroblasts, and a deposition of collagen.

Bronchitis as used herein is defined as an acute or chronic inflammation of any part of the bronchi and bronchial tubes. The bronchi are large delicate tubes in the lungs that are attached to the trachea and carry air to smaller tubes in the lungs. In bronchitis, including chronic bronchitis, there is mucous hypersecretion, an enlargement of tracheobronchial submucosal glands, and a disproportionate increase of mucous acini. Acute bronchitis is often characterized by fever, chest pain, severe coughing, and secretion of mucous material coughed up from the respiratory tract. Acute bronchitis affects the branches of the bronchi and may develop into bronchial or lobular pneumonia. Chronic bronchitis may result from repeated attacks of acute bronchitis. Consequently, a composition according to the present invention may be effective in controlling mucous hypersecretion, preventing, alleviating or treating an enlargement of tracheobronchial submucosal glands, and reduce and/or eliminate a disproportionate increase of mucous acini. The pathologic equivalent to chronic bronchitis is a non-specific series of changes in the bronchial wall generally characterized by an increase in the size and number of mucous glands and an increased number of goblet cells in the epithelium. When progressing into a chronic condition, bronchitis is a serious and incurable disorder. Consequently, a composition according to the present invention may be effective in controlling a series of changes in the bronchial wall generally characterized by an increase in the size and number of mucous glands and an increase in the number of goblet cells. A composition according to the present invention may also be capable of reducing and/or eliminating any mucos production including an increased mucos production.

Bronchial infections usually remain confined to the mucosa, and some resolve spontaneously without the need for treatment. Chronic bronchitis affects both the large and small airways. In the large airways, hypertrophy and hyperplasia of glandular structures and goblet cell metaplasia are prominent features of the condition. In the small airways, peribronchiolar fibrosis and airway narrowing may be prominent features. In chronic bronchitis hypertrophy of glandular structures and goblet cell metaplasia in the proximal airways likely contribute to an increased mucus production, the expectoration of which is one defining characteristic of chronic bronchitis. Consequently, a composition according to the present invention may be effective in preventing an airflow limitation in a subject prone to contracting bronchitis and/or to alleviate any airflow limitation or obstruction already present in said subject. Particularly, a composition according to the present invention may be effective in controlling hypertrophy and hyperplasia of glandular structures and goblet cell metaplasia, as well as peribronchiolar fibrosis and a narrowing of the small airways.

Bronchitis may be caused by a number of factors including viral and/or bacterial infection, environmental pollutants including cigarette smoke, and allergy. These factors may occur together or separately. A viral infection may e.g. predispose an individual to a subsequent bacterial infection. Bronchial infections occur in patients with abnormal airways who have reduced host defences. The three major bacterial pathogens isolated during bronchial infections are non-typable *Haemophlus influenzae, moraxella catarrhalis,* and *Streptococcus pneumoniae.* A composition according to the present invention may especially be effective in preventing viral and/or bacterial infection in a subject by e.g. increasing the host defences of said subject.

The term small airways as used herein is defined as small bronchi and bronchioles that contain no cartilage, glands or alveoli in their walls and measure 2 mm or less in internal diameter. The term small airways disease is used for a group of non-specific histological changes of peripheral airways found in individuals with a limited or obstructed airflow, including individuals having features such as mucus plugging, chronic inflammation, and muscular enlargement of small airway walls. Small airways disease is present in some patients with the clinical picture of chronic bronchitis. Consequently, a composition according to the present invention may be effective in treating, including prophylactically treating, alleviating and/or preventing a limited or obstructed flow of air through the small airways.

In small or peripheral airways disease, there is inflammation of bronchioli and mucous metaplasia and hyperplasia, increased intraluminal mucus and increased wall muscle. Consequently, a composition according to the present invention may be effective in controlling inflammation of the bronchioli and mucous metaplasia and hyperplasia, and effective in reducing and/or eliminating any increased intraluminal mucus formation and/or any increased wall muscle development.

DETAILED DESCRIPTION OF THE INVENTION

A composition according to the present invention comprises a novel combination of soy protein, preferably isolated soy protein, a phytoestrogen compound, preferably naturally occurring isoflavones, and dietary fibres, preferably soybean fibres, more preferably soy cotyledon fibres.

The soy protein can be provided by isolated soy protein, soy protein concentrate, soy flour or the like or any combination thereof. Isolated soy protein is preferred.

Isolated soy protein is the major proteinacious fraction of soybeans. It is prepared from high quality, dehulled, defatted soybeans by removing a preponderance of the non-protein components and the isolated soy protein fraction shall contain not less than 90 percent protein (N×6.25) on a moisture free basis. The preparation takes place through a series of steps in which the soybean protein portion is separated from the rest of the soybean. The removal of carbohydrate results in a product, which is essentially bland in flavour and therefore particularly useful in a nutritional composition for humans.

Soy protein concentrates are made by removing most of the oil and water-soluble non-protein constituents from defatted and dehulled soybeans. In the present context a soy protein concentrate shall preferably contain at least 65 percent protein on a moisture-free basis.

The soy protein can also be provided by soy flour, which can be full-fat or defatted soy flour. Full-fat soy flour comes from whole, dehulled soybeans that have been ground into a fine powder and, as the name implies, still contains the fat naturally found in soybeans. Defatted soy flour comes from whole, dehulled, defatted soybeans that have been ground into a fine powder. Soy flour is approximately 50 percent soy protein on a dry weight basis in the present context.

The soy protein used in a composition according to the present invention should preferably supply all the essential amino acids in the amounts required for humans. Preferably, the soy protein should also meet or exceed the essential amino acid requirement pattern for children and adults as established by the Food and Agricultural Organisation, World Health Organisation and United Nations University (FAO/WHO, UNU). Furthermore, the preferred soy protein should be comparable in digestibility to milk, meat, fish, and egg protein. Finally, the preferred soy protein shall be effective in maintaining nitrogen balance when consumed at the recommended protein intake level.

Preferred isolated soy protein products meeting the foregoing requirements are supplied by Protein Technologies International, Inc., under the brand name SUPRO®. SUPRO® isolated soy proteins are supplied in many different qualities and SUPRO® XT 12C is one particularly preferred quality. The currently most preferred quality is termed SUPRO® FXP-HO159.

The soy protein is preferably the main or sole protein source in a nutritional composition according to the present invention. However, parts of the protein source may be provided by other proteins such as e.g. skimmed milk, preferably as a powder, and other vegetable or animal proteins including diary proteins. Preferably, at least 45 weight percent, such as 50 weight percent, for example at least 60 weight percent, such as at least 70 weight percent, for example at least 75 weight percent, such as at least 80 weight percent, for example at least 85 weight percent, such as at least 90 weight percent, for example at least 95 weight percent, such as at least 98 weight percent of the total protein content of the composition is soy protein, and more preferably substantially all of the protein is soy protein.

In a preferred embodiment of the invention the soy protein is provided by isolated soy protein. In this embodiment, preferably at least 50 weight percent, for example at least 60 weight percent, such as at least 70 weight percent, for example at least 75 weight percent, such as at least 80 weight percent, for example at least 85 weight percent, such as at least 90 weight percent, for example at least 95 weight percent, such as at least 98 weight percent of the total protein content of the composition is isolated soy protein, and more preferably substantially all of the protein is provided by isolated soy protein.

The total protein content of a composition according to the present invention provides at least 15 percent of the total energy content of the composition, for example 18 percent, such as at least 20 percent, for example at least 22 percent, such as at least 25 percent, for example at least 28 percent, such as at least 30 percent, for example at least 32 percent, such as at least 35 percent, for example at least 38 percent, such as at least 40 percent, for example at least 42 percent, such as at least 45 percent, for example at least 48 percent, such as at least 50 percent of the total energy content of the composition, and preferably less than 90 percent of the total energy content of the composition.

Phytoestrogen compounds according to the present invention are defined as naturally occurring plant substances, said substances being either structurally or functionally similar to 17β-pestradiol or generating estrogenic effects. Phytoestrogens consist of a number of classes including isoflavones, coumestans, lignans and resorcylic acid lactones. Examples of isoflavones according to the present invention are genistein, daidzein, equol, glycitein, biochanin A, formononetin, and O-desmethylangolesin. The phytoestrogen compounds of a composition according to the present invention are preferably isoflavones, more preferably genistein, daidzein, glycitein and/or equol, yet more preferably genistein and/or daidzein, and even more preferably genistein. A preferred composition according to the present invention may accordingly comprise a single isoflavone, such as genistein, daidzein, glycitein or equol, or it may comprise at least one isoflavone selected from the group consisting of at least genistein, daidzein, glycitein and equol. When present in the plant the isoflavones are mainly in a glucoside form, i.e. attached to a sugar molecule. This glucoside form can be deconjugated to yield a so-called aglycone form, which is the biologically active species. A composition according to the present invention may comprise isoflavones in glucoside and/or aglycone forms regardless of whether the deconjugation to the aglycone form has taken place biologically, in vitro or by any other means whereby the isoflavones are included in a composition according to the present invention or if the aglycone forms are the native form of the isoflavones.

The phytoestrogen compound is preferably present in an amount of at least about 0.12 weight percent of the soy protein content, such as at least about 0.14 weight percent, for example at least about 0.16 weight percent, such as at least about 0.18 weight percent, for example at least about 0.20 weight percent, such as at least about 0.22 weight percent, for example at least about 0.24 weight percent, such as at least about 0.25 weight percent, for example more than about 0.25 weight percent, such as at least about 0.26 weight percent, for example at least about 0.28 weight percent, such as at least about 0.30 weight percent, for example at least about 0.32 weight percent, such as at least about 0.33 weight percent, for example more than about 0.33 weight percent, such as at least about 0.35 weight percent, for example at least about 0.40 weight percent, such as at least about 0.45 weight percent, for example at least about 0.50 weight percent, such as at least about 0.55 weight percent, for example at least about 0.60 weight percent, such as at least about 0.65 weight percent, for example at least about 0.70 weight percent, such as at least about 0.75 weight percent, for example at least about 0.80 weight percent, such as at least about 0.85 weight percent, for example at least about 0.90 weight percent, such as at least about 1.0 weight percent of the soy protein content, and preferably less than 2.50 weight percent of the soy protein content.

In the past, the downstream processing techniques used in the preparation of soy proteins have included steps that removed and/or destroyed isoflavones. Methods are available today, which provide soy protein products with high, fixed levels of naturally occurring isoflavones. The isoflavones according to the present invention in glucoside and/or aglycone forms can be included in a composition according to the present invention as part of such soy protein products and/or by themselves and/or as part of any other composition comprising isoflavones.

The dietary fibres used in the present invention should preferably comprise a mixture of insoluble fibres and water-soluble fibres also referred to as soluble fibres. Soluble fibres have a lowering effect on blood cholesterol levels. Examples of dietary fibres comprising soluble fibres are fibres from apples, bananas, oranges, carrots, oats, and soybeans. The dietary fibres preferably comprise soluble fibres in an amount of about 5 weight percent, such as about 10 weight percent, for example about 15 weight percent, such as about 20 weight percent, for example about 25 weight percent, such as about 30 weight percent, for example about 35 weight percent, such as about 40 weight percent, for example about 45 weight percent, such as about 50 weight percent, for example about 55 weight percent, such as about 60 weight percent, for example about 65 weight percent, such as about 70 weight percent, for example about 75 weight percent, such as about 80 weight percent, for example about 85 weight percent, such as about 90 weight percent, for example about 95 weight percent. The dietary fibres used in the present invention are preferably soybean fibres, more preferably soy cotyledon fibres. Such fibres are derived from dehulled and defatted soybean cotyledon and are comprised of a mixture of soluble and insoluble fibres. Soy cotyledon fibres are distinctly different from soybean fibres derived from soy hulls as well as other fibre sources. Soy cotyledon fibres are bland tasting, contain no cholesterol, are low in fat and sodium, and they have good water-binding properties and low caloric content.

Soy cotyledon fibres supplied in a fat-modified and low-cholesterol diet are known to further lower serum cholesterol levels in a subject suffering from mild to severe hypercholesterolemia. The effect is a lowering of the serum levels of total cholesterol including a lowering of LDL-cholesterol. However, HDL-cholesterol and total triglycerides are not significantly affected by soy cotyledon fibres. Soybean fibres, in particular soy cotyledon fibres, are believed to provide a synergistic effect in combination with soy protein and/or with a phytoestrogen compound, such as naturally occurring isoflavones, or to exert a potentiating effect on the soy protein and/or the phytoestrogen compound, said synergistic or potentiating effect being effective in lowering serum lipid and cholesterol levels in subjects having normal as well as elevated serum levels of total cholesterol and total triglycerides.

Without wishing to be bound by any specific theory it is presently believed that both soluble dietary fibres (working as nutrients) and insoluble dietary fibres (working as bulking agents), in particular from soybean fibres, more particularly soy cotyledon fibres, provide favourable growth conditions for the microflora in the human gut, which makes the microflora more effective in deconjugating isoflavones in the glucoside form to the aglycone form. Isoflavones in the aglycone form are absorbed faster and to a greater extent in the human gut than isoflavones in the glucoside form, and isoflavones in the aglycone form are the biologically more active species. In view hereof it can be understood that administration of a combination of soy proteins, a high, fixed level of isoflavones and a combination of soluble and insoluble fibres is effective in providing an increased uptake of isoflavones.

The amount of dietary fibres of the total weight of a composition according to the present invention on a dry basis is preferably more than 4 weight percent, for example at least 5 weight percent, such as at least 6 weight percent, for example at least 7 weight percent, such as at least 8 weight percent, for example at least 9 weight percent, such as at least 10 weight percent, for example at least 11 weight percent, such as at least 12 weight percent, for example at least 13 weight percent, such as at least 14 weight percent, for example at least 15 weight percent, such as at least 16 weight percent, for example at least 17 weight percent, such as at least 18 weight percent, for example at least 19 weight percent, such as at least 20 weight percent, and preferably less than 50 weight percent.

Preferred amounts of dietary fibres as a weight percent of the content of soy protein, shall be in the range of from about 10 to 100 weight percent, and preferred amounts are in the range of from 15 to 90 weight percent, such as from 20 to 80 weight percent, for example 25 weight percent, such as 30 weight percent, for example 33 weight percent, such as 35 weight percent, for example 40 weight percent, such as 50 weight percent, for example 60 weight percent, such as 70 weight percent, for example 75 weight percent.

Accordingly, the weight ratio of soy protein to dietary fibres is from about 1.0 to about 10.0, preferably more than about 1.0, for example about 1.25, such as at least about 1.5, for example at least about 1.75, such as at least about 2.0, for example at least about 2.25, such as at,least about 2.5, for example at least about 2.75, such as at least about 3.0, for example at least about 3.25, such as at least about 3.5, for example at least about 3.75, such as at least about 4.0, for example at least about 4.25, such as at least about 4.5, for example at least about 4.75, such as at least about 5.0, for example at least about 5.5, such as at least about 6.0, for example at least about 7.5.

The preferred daily dosage of soybean fibres is from at least 1 g to about 100 g soybean fibres, for example from at least 2 to about 75 g soybean fibres, such as from at least 3 g to about 50 g, for example from at least 4 g to about 40 g, such as from at least 5 to about 30 g, such as from at least 10 g to about 20 g soybean fibres.

Preferred soy cotyledon fibre products manufactured by Protein Technologies International, Inc. are marketed under the brand name of FIBRIM®. Among the various soybean fibres produced under the FIBRIM® brand, FIBRIM® 1020 is particularly preferred because of a particularly pleasant mouth feel and dispersability for dry blended beverage applications. FIBRIMO® 2000 is presently preferred for use in ready made liquids.

Two compositions of isolated soy protein and soy cotyledon fibre are preferred in order to maximise the content, of soy protein and isoflavones contained therein namely SUPRO®) FXP-HO159 and FIBRIM® 1020 for dry blended beverage applications and SUPROO® FXP-HO159 and FIBRIMO® 2000 for use in ready made liquids.

Alternatively, the present invention provides a composition wherein no soy protein is present and wherein the dietary fibres are soy cotyledon fibres. This composition provides soy cotyledon fibres in an amount of more than 4 weight percent of the total weight of the composition on a dry basis, and at least one phytoestrogen compound in an amount of more than 0.10 weight percent of the soy cotyledon fibres of the composition. The present invention also provides the use of such a composition as a medicament and/or in the manufacture of a medicament effective in treating and/or alleviating a pulmonary disease in a subject, said treatment and/or alleviation resulting in an increased $FEV_1$ of a subject, as measured by forced expiratory volume in the first second of expiration. The present invention also provides the use of such a composition and/or such a composition for use in treating pulmonary diseases in a subject.

When no soy protein is, present in the composition, the phytoestrogen compound is preferably present in an amount of at least about 0.12 weight percent of the soy cotyledon fibre content, such as at least about 0.14 weight percent, for example at least about 0.16 weight percent, such as at least about 0.18 weight percent, for example at least about 0.20 weight percent, such as at least about 0.22 weight percent, for example at least about 0.24 weight percent, such as at least about 0.25 weight percent, for example more than about 0.25 weight percent, such as at least about 0.26 weight percent, for example at least about 0.28 weight percent, such as at least about 0.30 weight percent, for example at least about 0.32 weight percent, such as at least about 0.33 weight percent, for example more than about 0.33 weight percent, such as at least about 0.35 weight percent, for example at least about 0.40 weight percent, such as at least about 0.45 weight percent, for example at least about 0.50 weight percent, such as at least about 0.55 weight percent, for example at least about 0.60 weight percent, such as at least about 0.65 weight percent, for example at least about 0.70 weight percent, such as at least about 0.75 weight percent, for example at least about 0.80 weight percent, such as at least about 0.85 weight percent, for example at least about 0.90 weight percent, such as at least about 1.00 weight percent, for example at least about 1.25 weight percent, such as at least about 1.50 weight percent, for example at least about 1.75 weight percent, such as at least about 2.00 weight percent, for example at least about 2.50 weight percent, such as at least about 3.00 weight percent, for example at least about 3.5 weight percent, such as at least about 5.00 weight percent of the soy cotyledon fibre content of the composition, and preferably less than 10.00 weight percent of the soy cotyledon fibre content of the composition.

Alternatively, the present invention provides a composition wherein no dietary fibres are present. This composition comprises soy protein, preferably isolated soy protein, in an amount of at least 50 weight percent of the total protein content of the composition, said total protein content providing at least 15 percent of the total energy content of the composition, and at least one phytoestrogen compound in an amount of more than 0.10 weight percent of the soy protein content of the composition. The present invention also provides the use of such a composition in the treatment and/or alleviation of a pulmonary disease in a subject, said treatment and/or alleviation resulting in an increased $FEV_1$ of a subject, as measured by forced expiratory volume in the first second of expiration. The present invention also provides the use of such a composition comprising soy protein and a phytoestrogen compound as a medicament and/or in the manufacture of a medicament effective in treating subjects diagnosed as having a pulmonary disease, said treatment being effective at least in increasing $FEV_1$ of a subject, as measured by forced expiratory volume in the first second of expiration. The present invention also provides the use of such a composition as a medicament and/or in the manufacture of a medicament effective in treating and/or alleviating pulmonary diseases in a subject.

A composition according to the present invention may optionally comprise a carbohydrate source, a fat source, flavouring agents, vitamins, minerals, electrolytes, trace elements and other conventional additives. The nutritional composition of the present invention may in one embodiment also comprise one or more flavouring agents such as cocoa, vanilla, lime, strawberry or soup flavours, such as mushroom, tomato or bouillon and sweeteners such as aspartame as well as other additives such as xanthan gum.

When a carbohydrate source is present in a composition according to the present invention, it is preferably present in an amount of less than 30 weight percent, such as less than 25 weight percent of the composition. Preferably, the amount of carbohydrate amounts to at least 5 weight percent, more preferred at least 10 weight percent, and most preferred at least 15 weight percent, of the composition. The preferred carbohydrates for use in the present invention are glucose, fructose and/or maltodextrine. Skimmed milk and cocoa are other possible carbohydrate sources.

When a fat source is present in a composition according to the present invention, it is usually present in an amount from 0.5 to 10 weight percent, preferably 1 to 9 weight percent, such as from 1.5 to 8 weight percent, for example from 2 to 7 weight percent, such as from 2.5 to 6 weight percent of the composition. The fat source will preferably comprise polyunsaturated fatty acids and monounsaturated fatty acids and optionally also saturated fatty acids. Soy lecithins and α-linolenic acid are particularly preferred. The fat source will preferably comprise polyunsaturated fatty acids and monounsaturated fatty acids and optionally also saturated fatty acids. The amount of polyunsaturated fatty acids and monounsaturated fatty acids, including the essential fatty acids, may range from 35 to 50, preferably 38 to 44, weight percent of the total amount of the fat source. The essential fatty acids are also called omega-6 and omega-3 fatty acids and include linolic acid and linolenic acid (α-linolenic acid). The amount of saturated fatty acids may be from 20 to 30 weight percent, preferably 22 to 26 weight percent, of the total amount of fat.

Vitamins and minerals may optionally be added to a composition according to the present invention in accordance with the limits laid down by health authorities. Preferably, a composition according to the present invention will comprise all recommended vitamins and minerals. The vitamins will typically include A, B1, B2, B12, folic acid, niacin, panthotenic acid, biotin, C, D, E and K. The minerals will typically include iron, zinc, iodine, copper, manganese, chromium and selenium. Electrolytes, such as sodium, potassium and chlorides, trace elements and other conventional additives may also be added in recommended amounts.

A preferred composition can be obtained by mixing:

|  | Content per 100 gram (%) | Grams per serving |
|---|---|---|
| Isolated soy protein (SUPRO ® FXP-HO159) | 50.00 | 18.5 |
| Soybean fibres (FIBRIM ® 1020) | 12.50 | 4.63 |
| Fructose | 22.62 | 8.37 |
| Lecithinated fat reduced cocoa | 9.30 | 3.44 |
| Soy lecithin | 3.55 | 1.31 |
| Flavourings | 1.28 | 0.47 |
| Xanthan gum | 0.50 | 0.19 |
| Aspartame | 0.25 | 0.09 |

The above-mentioned composition in an amount of preferably about 37 grams corresponds to one serving of a daily diet. The composition has an energy content of about 339 kcal (1,437 kJ) per 100 grams.

Another preferred composition can be obtained by mixing:

|  | Content per 100 gram (%) |
|---|---|
| Isolated soy protein (SUPRO ® FXP-HO159) | 50.00 |
| Soybean fibres (FIBRIM ® 1020) | 16.70 |
| Carbohydrates | 18.20 |
| Lecithinated fat reduced cocoa | 9.30 |
| Soy lecithin | 3.55 |
| Flavourings | 1.25 |
| Xanthan gum | 0.50 |
| Aspartame | 0.50 |

A composition according to the present invention may be used for special dietary use. For example, from one to three daily meals of ordinary food can be supplemented or replaced by a composition according to the present invention. The composition may provide from 50 to 200 kcal per serving.

The present invention also provides a composition according to the invention in the form of a micronutrient. In this connection a micronutrient is a nutritional supplement and/or a pharmacological composition and/or a medicament comprising i) a synthetic phytoestrogen-like compound capable of binding to an estrogen receptor or an estrogen-like receptor, and/or ii) a naturally occurring, plant-extractable compound in an amount, on a weight per weight basis, in excess of the amount of said compound, when it is present in a natural host such as a plant cell from which the compound can be extracted or isolated, and optionally iii) soy peptides obtainable from a partial hydrolysis of soy protein.

The naturally occurring, plant-extractable compound is preferably but not limited to compounds capable of binding to an estrogen receptor, an estrogen-like receptor, a beta-2-adrenergic receptor or a receptor belonging to the class of beta-2-adrenergic receptors. When the naturally occurring compounds are isolated from plants such as soybeans, they may be selected from the group at least containing phytoestrogens such as soybean phytoestrogens such as soybean isoflavones, soy protein or fragments thereof, e.g. peptides or amino acid sequences, soybean fibres, lecithin, linolenic acid, an antioxidant, a saponin, a lignan, a protease inhibitor, a trypsin inhibitor, and a tyrosine kinase inhibitor. Additional constituents of the micronutrient may preferably be selected among a DNA topoisomerase inhibitor, a ribosome kinase inhibitor, a growth control factor such as e.g. epidermal growth factor, transforming growth factor alpha, platelet derived growth factor, and preferably any growth. control factor controllable by a tyrosine kinase activity. The micronutrient may also comprise ormeloxifene and/or levormeloxifene as described by among others Holm et al. (1997) in Arteriosclerosis, Thrombosis, and Vascular Biology 17 (10), 2264–2272, and in Clinical Investigation, 100 (4), 821–828. When the naturally occurring compound is an isoflavone, the isoflavones may have been deconjugated to the aglycone form either biologically or in vitro prior to the incorporation in the micronutrient.

In one particularly preferred embodiment the present invention provides a composition or a micronutrient according to the present invention in combination with a functional food ingredient comprising a sterol, preferably an ingredient selected from the group consisting of a stanol ester, a tocotrienol, a mevinolin, and a phytosterol compound such as e.g. campesterbl, sitosterol or stigmasterol, or a combination thereof.

According to one preferred embodiment, a composition or a micronutrient according to the present invention is for use as a functional food ingredient. A composition or a micronutrient according to the present invention may also be administered as a probe or by intravenous administration, or in tablet or capsule form. The present invention also provides a pharmaceutical preparation comprising the a composition or a micronutrient according to the present invention, use of the a composition or a micronutrient according,to the present invention in therapy and/or a diagnostic method performed on the human or animal body, use of a composition or a micronutrient according to the present invention in the manufacture of a medicament and use of a composition or a micronutrient according to the present invention in the manufacture of a medicament for treating a subject suffering from a pulmonary disease.

The micronutrient is particularly useful in preventing and/or treating and/or prophylactically treating and/or alleviating a pulmonary disease such as e.g. a disease selected from the group consisting of inflammation of the airways, bronchoconstriction, bronchitis, asthma, and small airways diseases.

The present invention also provides a composition according to the present invention for use as a medicament and the use of a composition according to the present invention as a medicament and/or in the manufacture of a medicament for treating a subject suffering from a pulmonary disease, preferably a disease selected from the group consisting of inflammation of the airways, bronchoconstriction, bronchitis, asthma, and small airways diseases. Such a medicament may be effective in preventing and/or treating and/or prophylactically treating and/or alleviating a pulmonary disease such as e.g. a disease selected from the group consisting of inflammation of the airways, bronchoconstriction, bronchitis, asthma, and small airways diseases. The medicament is particularly effective in i) preventing and/or treating and/or prophylactically treating and/or alleviating asthma and/or ii) reducing and/or eliminating mucus hypersecretion and/or dyspnea in a subject suffering from asthma and/or iii) increasing $FEV_1$ of a subject as measured by forced expiratory volume in the first second of expiration and/or iv) preventing and/or treating and/or prophylactically treating and/or alleviating and/or reducing inflammation of the airways and/or v) preventing and/or treating and/or prophylactically treating and/or alleviating bronchoconstriction.

In a further aspect the present invention provides a method of preventing and/or treating and/or prophylactically treating and/or alleviating by therapy a pulmonary disease in a human or animal body, preferably a disease selected from the group consisting of inflammation of the airways, bronchoconstriction, bronchitis, asthma, and small airways diseases, said method comprising administration to said human or animal body of a composition according to the present invention in an amount effective in treating and/or preventing and/or prophylactically treating and/or alleviating inflammation of the airways and/or bronchoconstriction and/or bronchitis and/or small airways diseases and/or, asthma and/or reducing and/or eliminating mucus hypersecretion and/or dyspnea in a subject suffering from asthma and/or increasing $FEV_1$ of a subject as measured by forced expiratory volume in the first second of expiration.

In one embodiment the present invention provides a pharmaceutical preparation comprising a composition according to the present invention. The pharmaceutical preparation can be prepared in any way known to the skilled person.

In another embodiment the invention provides the use of a composition according to the present invention in the manufacture of a nutritional preparation for alleviating a pulmonary condition such as e.g. asthma. The nutritional preparation may take any form, which is suitable for human or animal consumption. In one preferred embodiment, the composition is a powdery mixture, which is suspendable, dispersible or emulsifiable in a liquid -for human or animal consumption. The liquid is preferably a water-containing liquid such as e.g. water, coffee, tea or fruit juice. For such a purpose, the composition is preferably packed in a package intended for covering the total nutritional requirement for a defined period of time, such as three days or a week.

The nutritional preparation in one embodiment of the present invention is preferably a functional food or drink, i.e. a readily obtainable edible or drinkable substance that is supplemented with a composition according to the present invention to provide a medical or pharmaceutical effect. Accordingly, the present invention provides a composition according to the present invention for use as a functional food ingredient. Functional foods and drinks are preferably-selected from the group consisting of diary products, such as yoghurt and yoghurt ice cream, juice, such as orange juice or tomato juice, ready made liquids for drinking, a spreadable product such as e.g. a margarine or a vegetable or plant extracted oil, a cereal product, such as a traditional breakfast cereal product, nutritional bars, biscuits, bread, soups, such as tomato soup, a meat product, such as a hamburger, a meat substitute product, and a vegetable product. In a further embodiment, a nutritional preparation according to the present invention may be in the form of a ready made liquid or in a powder form or in the form of a troche, a solid composition such as a nutritional bar, a fruit bar, a cookie, a cake, a bread or a muffin.

In another preferred embodiment, a composition according to the present invention is a liquid nutritional preparation in a water-containing liquid, in which the solid ingredients are suspended, dispersed or emulgated in an amount of from 10 to 25 weight percent. When the liquid nutritional preparation is intended for drinking, it will usually comprise a flavouring agent as discussed above. However, the liquid nutritional preparation may also be used for probe administration.

EXAMPLE 1

A 52 years old man, who had suffered from chronic asthma for many years, was treated with two daily supplements of a composition according to the invention comprising isolated soy protein, isoflavones and soy cotyledon fibres. The daily dose of isolated soy protein was 25 g and the daily dose of soy cotyledon fibres was 8 9. This treatment led to a reduced intake of medicine and a substantial clinical improvement with fewer and less severe attacks of asthma and improved lung capacity.

EXAMPLE 2

A 19 years old man, who suffered from chronic asthma, received the same dosage of the same composition as the subject in Example 1. This led to reduced intake of medicine and substantially improved capacity to perform physical activity. This subject was for the first time in years able to run and play football, which in the past immediately and inevitably provoked attacks of asthma.

What is claimed is:

1. A method of treating a disease in a human or animal body, said method comprising administering to said human or animal body an effective amount of a composition comprising (a) a soy protein source, selected from the group consisting of isolated soy protein, soy protein concentrate and soy flour, said soy protein source providing an amount of soy protein, which is least 45 weight percent of the total protein content of the composition, said total protein content providing at least 15 percent of the total energy content of the composition, (b) at least one phytoestrogen compound in an amount of more than 0.10 weight percent of the soy protein content of the composition, and (c) dietary fibres in an amount of more than 6 weight percent of the total weight of the nutritional composition on a dry basis, said disease being selected from inflammation of the airways, bronchoconstriction, bronchitis, asthma, small airways diseases, mucus hypersecretion and dyspnea.

2. A method according to claim 1 wherein the disease is selected from the group consisting of inflammation of the airways, bronchoconstriction, bronchitis, asthma, and small airways diseases.

3. A method according to claim 1 wherein the composition is effective in treating asthma.

4. A method according to claim 1 wherein the composition is effective in reducing or eliminating mucus hypersecretion or dyspnea in a human or animal suffering from asthma.

5. A method according to claim 1 wherein the composition is effective in increasing $FEV_1$ of a human or animal as measured by forced expiratory volume in the first second of expiration.

6. A method according to claim 1 wherein the composition is effective in reducing inflammation of the airways.

* * * * *

UNITED STATES PATENT AND TRADEMARK OFFICE
CERTIFICATE OF CORRECTION

PATENT NO. : 6,509,043 B1  Page 1 of 2
DATED : January 21, 2003
INVENTOR(S) : Høie It is certified that error appears in the above-identified patent and that said Letters Patent is hereby corrected as shown below:

Title page,
Item [56], FOREIGN PATENT DOCUMENTS, "WO 98 31546" should be
-- WO 97 31546 --.
OTHER PUBLICATIONS, "vol. 15, No.5" should be -- vol. 15, No. 6 --.

Column 3,
Line 15, "Gooderham (J. Nutr....." should begin a new paragraph.

Column 4,
Line 15, "7O-glucoside" should be -- 7-O-glucoside --.
Line 16, "acetyidiadzin" should be -- acetyldiadzin --.
Line 18, "malonyidiadzin" should be -- malonyldiadzin --.

Column 5,
Line 24, "edible-product" should be -- edible product --.
Line 67, "$38_{th}$" should be -- $38^{th}$ --.

Column 7,
Line 56, "17β-testradiol" should be -- 17β-estradiol --.

Column 8,
Lines 34-35 and 63, "is:defined" should be -- is defined --.
Line 48, "airways'" should be -- airways --.

Column 11,
Line 59, "result's" should be -- results --.

Column 15,
Line 61, "17β-pestradiol" should be -- 17β-estradiol --.

Column 18,
Line 34, "SUPRO® )" should be -- SUPRO® --.
Line 35, "SUPROO® " should be -- SUPRO® --.
Line 54, "is, present" should be -- is present --.

Column 21,
Line 29, "growth. control" should be -- growth control --.

Column 22,
Line 53, "-for" should be -- for --.

UNITED STATES PATENT AND TRADEMARK OFFICE
CERTIFICATE OF CORRECTION

PATENT NO.     : 6,509,043 B1
DATED          : January 21, 2003
INVENTOR(S)    : Høie It is certified that error appears in the above-identified patent and that said Letters Patent is hereby corrected as shown below:

<u>Column 23,</u>
Line 30, "8 9" should be -- 8 g --.

Signed and Sealed this

Eighth Day of July, 2003

JAMES E. ROGAN
*Director of the United States Patent and Trademark Office*